United States Patent
Louis Dit Picard et al.

(10) Patent No.: US 7,488,697 B2
(45) Date of Patent: Feb. 10, 2009

(54) SKIN CARE ARTICLE

(75) Inventors: Bernard Louis Dit Picard, Amfreville la Campagne (FR); Philippe Gregoire, Les Andelys (FR)

(73) Assignee: Georgia-Pacific France (FR)

( * ) Notice: Subject to any disclaimer, the term of this patent is extended or adjusted under 35 U.S.C. 154(b) by 141 days.

(21) Appl. No.: 10/574,126

(22) PCT Filed: Sep. 30, 2004

(86) PCT No.: PCT/FR2004/002475

§ 371 (c)(1),
(2), (4) Date: Mar. 31, 2006

(87) PCT Pub. No.: WO2005/033392

PCT Pub. Date: Apr. 14, 2005

(65) Prior Publication Data

US 2007/0000082 A1    Jan. 4, 2007

(30) Foreign Application Priority Data

Oct. 2, 2003   (FR) .................................. 03 11560

(51) Int. Cl.
*B32B 5/26* (2006.01)
*B32B 7/08* (2006.01)

(52) U.S. Cl. ...................... 442/381; 442/384; 442/387; 604/358; 604/374; 428/98; 428/141; 428/167; 428/170; 428/171; 428/172; 15/208

(58) Field of Classification Search ................. 442/381, 442/384, 387; 428/98, 141, 167, 170–172
See application file for complete search history.

(56) References Cited

U.S. PATENT DOCUMENTS

| | | | |
|---|---|---|---|
| 5,437,372 A | 8/1995 | Per-Lee | |
| 2002/0064639 A1 * | 5/2002 | Rearick et al. | 428/292.1 |

FOREIGN PATENT DOCUMENTS

| | | |
|---|---|---|
| EP | 0405043 A1 | 1/1991 |
| EP | 0851052 A1 | 7/1998 |
| EP | 1167605 A1 | 1/2002 |
| FR | 2052089 | 4/1971 |
| FR | EP 826811 * | 3/1998 |
| WO | WO 94/02674 | 2/1994 |
| WO | WO 00/76384 A1 | 12/2000 |

* cited by examiner

*Primary Examiner*—Lynda Salvatore
(74) *Attorney, Agent, or Firm*—Joel T. Charlton

(57) ABSTRACT

The invention relates to a skin care article exhibiting a scrub cleaning effect by friction and comprising at least one first and one second external layer made of a fibrous material. The inventive article is characterized in that the first layer (10, 10', 10") forms an absorbing cushion and substantially consists of low-micronaire cellulose fibers, in particular less than 8, and the second layer (20, 20', 20") is substantially consists of high-micronaire fibers, in particular of micronaire higher than 8, said layers being selected from the following materials: flax, ramie, sisal, jute and hemp separate or mixed.

22 Claims, 1 Drawing Sheet

SKIN CARE ARTICLE

This invention relates to an article, made mainly of fibers, intended for cosmetic skin care and having in particular the property of possessing an exfoliating effect.

In the skin care industry, in the field of cosmetic products in particular, exfoliation or scrubbing treatment is known. This operation makes it possible, by a mechanical rubbing action, to eliminate impurities encrusted and accumulated on the surface of the epidermis and dead cells as well. Rubbing makes it possible to improve the texture of the skin, purify the epidermis, and clear up the complexion. Usually natural fibers are used. We know, for example, of the luffa or dishcloth gourd sponge, the horsehair, hemp, or even sisal glove. However, these coarse fibers used in this form result in a strong scrubbing that can only be performed from time to time, on a weekly or even monthly basis. We also know of exfoliating preparations with natural, organic, or plant-type ingredients, such as strawberry achenes, crushed apricot pits, organic bamboo silica, gourd cellulose, or even mineral-type ingredients, such as silica beads or even artificial and/or synthetic ingredients. The latter include all polymers, such as polyethylene, polyamide 6.6, polypropylene, EVA, etc.

Currently proposed are disk-shaped pads made of an absorbent substrate in a spongy or fibrous material, comprising on its surface ingredients having an exfoliating effect. For example, U.S. Patent Application No. 2002/0087167 describes such a skin cleansing article with an abrasive sheet on its surface. This sheet, consisting of a cotton or flax or equivalent fabric, supports fine grains of sand or some other abrasive material, scattered on its surface. The grains are chosen for their use in microdermo-abrasion. These are microbeads that lend themselves to gentler scrubbings. Breakable spheres that release active principles are also added to said microbeads. However, in the case of a fibrous substrate, incorporation of a material in particle form and bonding of said particles to the fibers are factors that make for a more complex manufacturing process and thus limit production rates. For example, special attention must then be paid to the processing of scraps from cutting of the lap into individual pads. The recycling of said scraps creates a problem because they are likely to contaminate the fibers due to their abrasive particles.

The object of the invention is to create a product having both a scrubbing action and some ability to absorb liquids.

The object of the invention is also to create a product intended for skin care and having a scrubbing action due solely to textile techniques while permitting the recycling of scraps.

In particular, the object of the invention is a product that can be manufactured on existing equipment for the manufacture of products made of cotton or made of a blend of cotton-substituting fibers without requiring major modifications for said equipment.

Another object of the invention is a product that can be made solely of natural cellulose fibers.

These objects can be attained according to the invention with a skin care article, in particular an article for cosmetic skin care, having an exfoliating effect produced by rubbing and comprising at least one first and one second layer of fibrous materials, in particular cellulose fibers, characterized in that the first layer forms an absorbent mat and is comprised essentially of cellulose fibers with a low micronaire, in particular a micronaire lower than 8, while the second layer is comprised essentially of fibers with a high micronaire, in particular a micronaire higher than 8, said fibers being selected from among the following materials: flax, ramie, sisal, jute, hemp, either individually or as a blend.

In particular, the second layer comprises at least 50%, preferably 70%, high-micronaire fibers, and at the most 50%, preferably 30%, other fibers, whether natural, synthetic or artificial.

The first layer comprises at least 50%, in particular at least 70%, and more specifically 100%, of the said cellulose fibers.

Preferably, the layers are bonded to each other. The layers are advantageously bonded according to a hydraulic bonding technique called hydroentangling. The product thus obtained has a breaking strength ranging from 10 to 60 N for a specimen 25 mm wide.

Thanks to the invention, a product is created exhibiting one part capable of absorbing liquids with its hydrophilic cotton fibers, possibly combined with others such as artificial and/or synthetic fibers, and another part with a slightly abrasive action on the skin due to its high-micronaire fibers. The overall product surprisingly exhibits, after bonding of the fibers, a perfect cohesion.

The applicant is the owner of EP Patent 0 951 582. Said patent relates to a hydrophilic cotton product made of 100% cotton fibers and comprising a first layer made of fine fibers with a low micronaire value and forming a soft facing, as well as a second outside layer made of fibers with a higher micronaire value and forming an abrading facing. The above-mentioned values are a micronaire value ranging from 2 to 5 μg/inch for the first layer, and a micronaire value ranging from 4 to 10 μg/inch for the second layer. Actually, in practice, the micronaire value of the second layer remains less than 8.5 μg/inch, since cotton only exceptionally has a micronaire value higher than 7.5. We should note that usually, when reference is made to the micronaire value, the μg/inch unit is not mentioned. The product according to the patent is intended for a cosmetic use for applying and/or removing makeup on the skin.

This invention differs from the above prior art in that the pad is not solely intended for a simple skin cleansing as performed at the time of makeup removal. While the characteristics of the pad according to that prior art make it possible to remove foundation, rouge, lipstick or other makeup products, said characteristics are not suited to a scrubbing operation involving the abrasive properties of the substrate. We were surprised to find that a fibrous pad could be conferred, in addition to its makeup removal function, a skin scrubbing function by simply substituting part of the cotton fibers with larger and more rigid high-micronaire fibers.

Furthermore, this new product is obtained without having to substantially modify the industrial pad-making equipment. This is particularly advantageous when one wishes to manufacture products that are efficient, low-cost, and intended for mass distribution.

Additionally, it should be noted that in the case of flax fibers, the high micronaire value results from the accumulation of fibers rather than from the fineness of the individual fiber. As presented hereinafter, the conventional boil-off and bleaching process, as applied to cotton, does not yield a fiber separation sufficient to individualize them.

The invention is described in greater detail below with reference to the attached drawings, wherein FIG. 1 represents in cross-section an example of an embodiment of one article of the invention;

Figure 1:
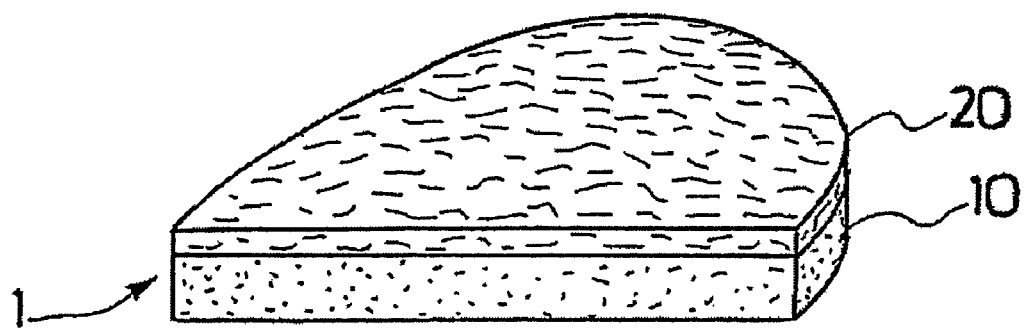

As can be seen in FIG. 1, the article or pad 1 marketed for a cosmetic use that includes a skin scrubbing operation forms a disk or a format with any contour. The contour may be circular, oval, polygonal, or of any other shape. The pad comprises a first fibrous layer 10 forming a liquid-absorbent mat. The mat is essentially made of bleached cotton fibers. The fibers may be partly blended with other fibers commonly used in the field of cosmetic-use articles, such as artificial fibers like viscose, or even synthetic fibers, whether or not hydrophilic. Depending on the pad-cutting technique used, part of the initial lap may be recycled. These recycled fibers are then incorporated into the new fibers comprising the first layer. The amount of non-cotton fibers is preferably limited to 50%, and more specifically 30%, of the total fibers in the layer.

The lap weight ranges from 30 to 300 g/m$^2$. The lap may be an air-laid lap formed by a machine of the Rando Webber type that arranges the fibers with a certain inclined orientation relative to the lap-forming direction. Consequently the layer is relatively thick. The lap may be joined with one or several carded webs, as in the lap formed according to the continuous bleaching process and described in the applicant's EP Patent 0 681 621.

This layer may also be entirely manufactured from one or several cards, and thus comprise a set of carded webs.

Owing to the bleached hydrophilic cotton fibers, the mat absorbs very well the products used in makeup application, makeup removal, or other skin care operations.

The second layer 20 is made of high-micronaire fibers, said micronaire being greater than 8. These are preferably natural fibers, advantageously chosen from among flax, hemp, sisal, jute or ramie, either individually or as a blend. The fibers are also bleached. The weight of the second layer preferably ranges from 15 to 120 g/m$^2$. The fibers together form a thin lap obtained by a known lap-making machine. The fibers may also be arranged into one or several superimposed carded webs. The layer 20 can also be manufactured using the air-laid method. The second layer is preferably made exclusively of high-micronaire fibers such as flax, however, it may comprise other fibers in a minority proportion.

In the case of flax, the fibers individually have a diameter ranging from 0.015 to 0.025 mm. Said diameter differs little from that of cotton fibers, which ranges from 0.015 to 0.04 mm. However, due to the pectic matters that glue together the fiber bundles, flax fibers are difficult to individualize with conventional cotton bleaching processes. They form clusters or shives. The actual diameter of the clusters looks bigger, and they are more rigid than the fibers themselves. While the micronaire value of cotton generally ranges from 2 to 8 depending on the fiber's origin, the micronaire value of bleached flax fibers is greater than 8. This property is often exploited to create a layer with an exfoliating effect. The embodiment of the invention is extended to natural fibers whose micronaire is greater than 8 after they are bleached under standard cotton bleaching conditions. For example, no additional carding is performed after boiling off and bleaching. The natural fibers involved are sisal, hemp, jute, or ramie.

We should note that the micronaire value represents the mean mass of the fibers per unit of length, in μg/inch, of a sample of fibrous matter product being tested. This value is directly related to the mean section of fibers or fiber cluster. Said value defines the fineness of fibers or fiber clusters and is measured with a measuring instrument, such as the SHEFFIELD Micronaire, in accordance with an established method, for example, the ISO 2403 or NF G 07-073 method.

The measurement of fiber fineness is based on the air permeability of a mass of fibers under certain specific conditions, according to an arbitrary scale called the micronaire scale. The air permeability of a given sample is measured, which sample is taken from an external layer of the product according to the invention (constituting the test specimen), by reading the resistance to air flow on the air flow instrument, on a scale graduated with respect to air flow variations or pressure differences. Said scale was previously calibrated with a series of reference cottons.

The equipment includes a scale for measuring the mass of the specimen, an air flow instrument for measuring the micronaire value, which air flow instrument consists in a perforated compression cylinder containing the test specimen and those devices necessary for measuring the air permeability of the specimen, such as an air pump, means for regulating the air flow or pressure through the specimen in the compression cylinder, a manometer for reading the required difference in pressure, and a flowmeter for reading the air flow through the specimen as well as, if necessary, a scale graduated in micronaire value or a conversion table for converting the reading values into micronaire values. Sampling and specimen-taking are performed, for example, in accordance with Standards NF G 07-050 and NF G 07-062.

Next the specimen mass is determined. The specimen is introduced, evenly and in small amounts, into the compression cylinder, then the fiber compression piston is set in place and locked. The air intake is opened at the appropriate pressure or flow, and the difference in pressure is noted on the scale of the instrument.

For air flow instruments with a scale graduated in micronaire values, the mean of readings obtained for the whole set of specimens taken from the same sample is computed. For air flow instruments with a scale graduated in units other than micronaire values, the direct readings are converted into micronaire values by using the conversion curve.

The micronaire value, representing the mean mass of fibers at the unit of length, is expressed in μg/inch.

The layers 10 and 20 are advantageously bonded to each other. They may have undergone a mechanical or hydraulic entangling. The process preferably involves bonding by means of water jets. The energy applied by the jets onto the facing comprising the second layer ranges from $0.7 \times 10^{-3}$ and $10 \times 10^{-3}$ kWh/m$^2$, depending on the condition of the lap fibers during processing.

Surprisingly, it was found that pads exhibiting such a structure held up very well and had a higher breaking strength than expected. The latter property is important in an application where the pad will be rubbed on the skin. Said pad then better fulfills its surface cleansing function and sheds less fibers due to fluffiness.

Among high-micronaire fibers, it is known for example that flax enjoys a higher dry tenacity than cotton. Said dry tenacity ranges from 40 to 60 g/tex versus a range of 25 to 40 g/tex for cotton. Furthermore, its wet tenacity, a primary condition of its use, is greater by 50 to 80% relative to the dry tenacity.

Thus a pad of 250 g/m$^2$ grammage and entirely made of cotton was compared in dry to another pad comprising a cotton mat of the same grammage to a carded web layer of 40 g/m$^2$ grammage and made of flax fibers.

The first pad exhibited a machine-direction breaking strength of 17 N, while the breaking strength of the second pad was as high as 40 N. This is beyond the expected value which was no more than 30 N taking into account the grammage difference.

Figure 2:
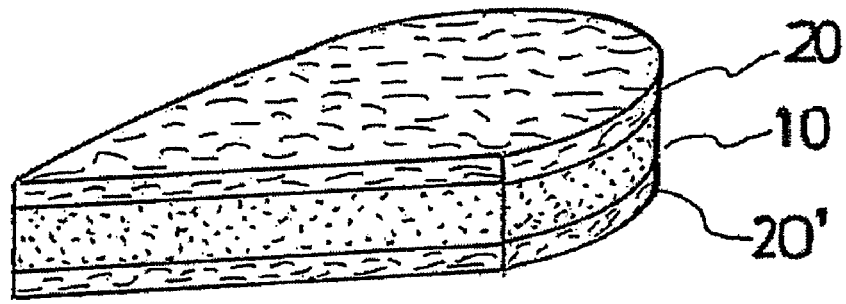
FIG. 2 represents a second embodiment of the invention.

FIG. 2 shows another embodiment in which the first absorbent layer 10, essentially made of cotton fibers, is sandwiched between two layers 20 and 20' made of high-micronaire fibers, such as flax. The first layer has a grammage ranging from 30 to 300 g/m², while each of the two flax-fiber layers has a grammage ranging from 15 to 120 g/m², as in the first embodiment.

Figure 3:
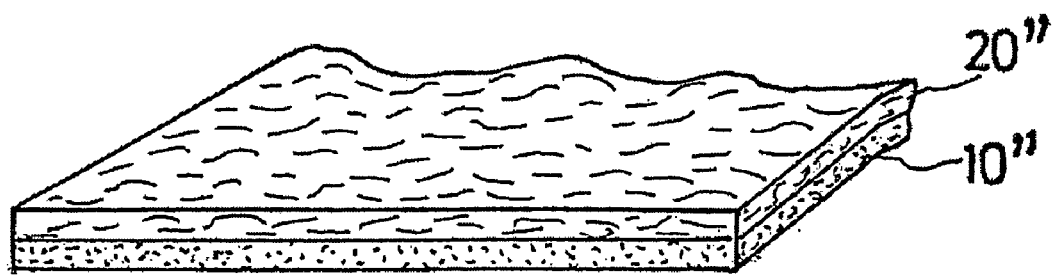
FIG. 3 represents a third embodiment of the invention.

FIG. 3 shows another embodiment in the form of a lightweight nonwoven, having a grammage of 45 to 100 g/m², with one cotton layer 10" and one high-micronaire-fiber layer 20". The layers essentially have the same thickness, which is low. This nonwoven, due to its application in a cosmetic use, may or may not be soaked in a therapeutic or makeup-removal lotion. This type of product is known in the cosmetic industry as a makeup-removal or exfoliating wipe.

In order to manufacture a pad or a wipe in accordance with the invention, using textile lap-making means known in themselves, a fibrous lap is prepared whose grammage preferably ranges from 30 to 300 g/m². The lap advantageously comprises at least 70% bleached cotton fibers. The fibers most often used with cotton are viscose or polyester. On top of this first fibrous layer, a second layer is placed, which second layer comprises one or more carded webs made of high-micronaire bleached natural fibers, for example bleached flax. The grammage of this second layer ranges from 15 to 120 g/m². If applicable, a third layer of high-micronaire bleached natural fibers is placed onto the opposite facing of the cotton lap.

The whole product is guided through an interfacial bonding of layers and consolidation station. This advantageously involves bonding by means of water jets. A known hydroentangling process consists in subjecting the fibrous structure to high-pressure water jets in order to entangle all or part of the fibers and to modify some of its characteristics. This process seeks in particular to modify the mechanical strength and fluffiness. The fibrous lap is supported by a porous cloth that moves in a direction perpendicular in relation to the water jets. Said water jets are produced by an apparatus comprising one or several rows of injectors arranged crosswise relative to the displacement direction of the fibrous lap. Usually the injectors are created by machining circular-shaped calibrated perforations, all having the same diameter and an appropriate profile, in a metal sheet. The metal sheet fully covers a distribution channel fed by pumps that supply water at high pressure.

For the application described herein, the water jets are installed for supplying an energy of $6.6 \times 10^{-3}$ kWh/m² for the flax facing, and $0.9 \times 10^{-3}$ kWh/m² for the other facing. The fibers become entangled under the action of the jets. The perforations commonly have a diameter ranging from 80 μm to 200 μm and are spaced lengthwise on the metal sheet. The spacing ranges from 0.5 to 8 mm. Metal sheets exhibiting one to three rows of perforations can be found in the trade.

The porous cloth on which the fibrous lap is spread is driven along a planar table or even on a cylinder put into rotation. The porous cloth enables the water to cross the fibrous lap, and a water suction means contrived underneath the cloth ensures its discharge.

Beyond a certain grammage or thickness of the lap, this apparatus has the immediately visible result of creating a raised relief formed by continuous, straight lines parallel to each other. These lines are aligned in the direction of scrolling of the lap in relation to the injectors.

The lap may be consolidated by other known means such as, for example, calendering, mechanical entangling, or even thermal processing combined with the incorporation of powders or fusible fibers. If applicable, the lap is dried. Next, the lap is cut into pads or individual formats. The cutting means can be, for example, cutting dies or knives mounted onto rotating cylinders.

According to another embodiment, the manufacturing process involves preparing a first cotton-fiber layer on the one hand, and at least one second layer of natural fibers chosen from among flax, sisal, hemp, jute and ramie in the form of carded webs on the other hand. The fibers are unbleached; they have not yet undergone any chemical boil-off and bleaching process. The lap comprising various layers is subjected to boil-off and bleaching liquids, either in a continuous process as described in the patent filed by the applicant, namely EP Patent 0 524 268, or in a discontinuous process in accordance with traditional techniques or as described in Patents Nos. EP 0 735 175 and FR 2 552 120.

The bonding operation, advantageously involving water jets, is performed prior to or subsequent to the chemical processing.

These techniques, as described in the above-mentioned patents, ensure an excellent cohesion of fibers within each layer and between the layers, thus contributing to the creation of a product that is remarkably homogeneous as regards its appearance.

The invention claimed is:

1. An article for skin care for providing an exfoliating effect comprising at least one first layer of fibrous material and one second layer of fibrous material, wherein the first layer is an absorbent lap comprising cellulose fibers having a micronaire lower than 8, wherein the second layer comprises cellulose fibers having a micronaire higher than 8, said cellulose fibers of said second layer being selected from flax, ramie, sisal, jute or hemp, either individually or as a blend.

2. The article according to claim 1, wherein said second layer comprises at least 50% high-micronaire fibers, and at the most 50% of other fibers.

3. The article according to claim 1, wherein said first layer comprises at least 50% of said cellulose fibers.

4. The article according to claim 3, wherein said cellulose fibers of said first layer are cotton.

5. The article according to claim 1, wherein grammage of the first layer is between 30 and 300 g/m².

6. The article according to claim 3, wherein said first layer includes up to 50% of synthetic and/or artificial fibers.

7. The article according to claim 3, wherein said first layer comprises a sheet of fibers formed by an air-laid means or by carding.

8. The article according to claim 1, wherein said first layer includes one or more superimposed carded webs.

9. The article according to claim 1, wherein grammage of the second layer is between 15 and 120 g/m².

10. The article according to claim 1 further comprising a third layer including fibers having a high micronaire, the first layer being arranged between the second layer and the third layer.

11. The article according to claim 1, wherein cellulose fibers of the second layer are flax.

12. The article according to claim 10, wherein said second layer and/or the third layer are formed by carded webs.

13. The article according to claim 10, wherein said second layer or said third layer are a sheet formed by an air-laid means.

14. The article according to claim 1, wherein the first layer and the second layer are bonded together.

15. The article according to claim 14, wherein said first layer and the second layer are bonded together by hydroentangling.

16. The article according to claim 14, wherein breaking strength is between 10 N and 60 N for a specimen 25 mm wide.

17. The article according to claim 15, wherein breaking strength is between 10 N and 60 N for a specimen 25 mm wide.

18. The article according to claim 16, wherein said article is a wipe with a grammage of between 45 and 100 g/m$^2$.

19. The article according to claim 17, wherein said article is a wipe with a grammage of between 45 and 100 g/m$^2$.

20. A process for manufacturing an article according to claim 15, wherein hydroentangling energy applied to a facing of the second layer ranges from $0.7 \times 10^{-3}$ and $10 \times 10^{-3}$ kWh/m$^2$.

21. The process according to claim 20, wherein said first layer and said second layer are formed from unbleached natural fibers and are hydroentangled before undergoing any chemical treatment of bleaching or boiling off.

22. The process according to claim 20, wherein said first layer and said second layer are formed from unbleached natural fibers and are bleached or boiled off before being hydroentangled.

* * * * *